(12) United States Patent
Kitajima

(10) Patent No.: US 9,936,141 B2
(45) Date of Patent: Apr. 3, 2018

(54) IMAGE PROCESSING APPARATUS FOR PERFORMING CORRECTION PROCESSING FOR EFFECTING VIRTUAL LIGHT SOURCE AND METHOD EXECUTED BY IMAGE PROCESSING APPARATUS

(71) Applicant: CANON KABUSHIKI KAISHA, Tokyo (JP)

(72) Inventor: Kotaro Kitajima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 116 days.

(21) Appl. No.: 14/927,634

(22) Filed: Oct. 30, 2015

(65) Prior Publication Data
US 2016/0127630 A1    May 5, 2016

(30) Foreign Application Priority Data
Nov. 5, 2014 (JP) ................. 2014-225436

(51) Int. Cl.
| | |
|---|---|
| *H04N 5/232* | (2006.01) |
| *H04N 5/262* | (2006.01) |
| *G06T 5/00* | (2006.01) |
| *G01N 21/88* | (2006.01) |
| *H04N 5/235* | (2006.01) |

(52) U.S. Cl.
CPC ........... *H04N 5/2351* (2013.01); *G06T 5/008* (2013.01); *H04N 5/2354* (2013.01); *H04N 5/2621* (2013.01); *G01N 2021/8838* (2013.01)

(58) Field of Classification Search
CPC ............... H04N 5/2351; H04N 5/2256; G01N 2021/8838; G06T 5/008
See application file for complete search history.

(56) References Cited

U.S. PATENT DOCUMENTS

2006/0269270 A1* 11/2006 Yoda ..................... G03B 15/03
                                                              396/155

FOREIGN PATENT DOCUMENTS

JP          2005-167376 A      6/2005

\* cited by examiner

*Primary Examiner* — Ahmed A Berhan
(74) *Attorney, Agent, or Firm* — Cowan, Liebowitz & Latman, P.C.

(57) ABSTRACT

The amount of light to be emitted by an auxiliary light source for capturing an image to which correction processing is applied, as well as a parameter used in the correction processing, is determined based on a degree of shadows of an object to be captured using the auxiliary light source. In this way, shadows in an image obtained through image capture using the auxiliary light source can be appropriately corrected with a simple method.

18 Claims, 11 Drawing Sheets

NO LIGHT EMISSION BY
AUXILIARY LIGHT SOURCE

AFTER LIGHT EMISSION BY
AUXILIARY LIGHT SOURCE
(NORMAL LIGHT EMISSION)

AFTER GAIN PROCESSING

AFTER LIGHT EMISSION BY
VIRTUAL LIGHT SOURCE

NO LIGHT EMISSION BY
AUXILIARY LIGHT SOURCE

AFTER LIGHT EMISSION BY
AUXILIARY LIGHT SOURCE
(WEAK LIGHT EMISSION)

RELIGHTING

AFTER RELIGHTING

IMAGE PROCESSING APPARATUS FOR PERFORMING CORRECTION PROCESSING FOR EFFECTING VIRTUAL LIGHT SOURCE AND METHOD EXECUTED BY IMAGE PROCESSING APPARATUS

BACKGROUND OF THE INVENTION

Field of the Invention

The present invention relates to an image capture apparatus and a method executed by the image capture apparatus, and more particularly to an image capture apparatus that can handle images captured using an auxiliary light source and a method executed by the image capture apparatus.

Description of the Related Art

It is known that noise increases and the image quality is degraded with an increase in the film speed at the time of image capture in a dark scene, and with an increase in pixel values in an attempt to brighten a dark image that has been captured in an underexposure state. Therefore, when the amount of light used in lighting up an object is not sufficient, the amount of light is generally supplemented with the aid of an auxiliary light source, such as a flash, during image capture. However, in a case where the object is lit up at its front by auxiliary light during image capture, e.g., in a case where an auxiliary light source built in a camera is used, there is a possibility that the resultant image undesirably looks flat with few three-dimensional characteristics due to reduced shadows on the object.

To address this issue, a first embodiment of Japanese Patent Laid-Open No. 2005-167376 discloses a camera that is provided with a plurality of auxiliary light sources with different light emission directions, and that presents, in a selectable manner, images obtained by performing image capture with the auxiliary light sources emitting light on an individual basis.

The method described in Japanese Patent Laid-Open No. 2005-167376 enables a user to select an image of an object with shadows that the user likes, from among the results of image capture using the auxiliary light sources. However, the necessity to provide the camera with the plurality of auxiliary light sources leads to an increase in cost of the camera. Furthermore, as the frequency of required image capture increases with a larger number of auxiliary light sources, it takes time to select a final image. Moreover, if the object moves, e.g., closes its eyes while performing image capture multiple times, there is a possibility that a desired image cannot be obtained.

SUMMARY OF THE INVENTION

The present invention has been made in view of the foregoing problems of a conventional technique, and provides an image capture apparatus that can appropriately correct shadows in an image obtained through image capture using an auxiliary light source with a simple method, as well as a method executed by the image capture apparatus.

According to an aspect of the present invention, there is provided an image capture apparatus, comprising: an application unit configured to apply, to an image captured using an auxiliary light source, correction processing for adding an effect of a virtual light source; and a determination unit configured to determine an amount of light to be emitted by the auxiliary light source for capturing the image to which the correction processing is applied, and determine a parameter used in the correction processing, wherein the determination unit determines the amount of light to be emitted and the parameter based on a degree of shadows of an object to be captured using the auxiliary light source.

According to another aspect of the present invention, there is provided a method executed by an image capture apparatus, the method comprising: applying, to an image captured using an auxiliary light source, correction processing for adding an effect of a virtual light source; and determining an amount of light to be emitted by the auxiliary light source for capturing the image to which the correction processing is applied, and determining a parameter used in the correction processing, wherein in the determining, the amount of light to be emitted and the parameter are determined based on a degree of shadows of an object to be captured using the auxiliary light source.

According to a further aspect of the present invention, there is provided a non-transitory computer-readable recording medium storing a program for causing a computer provided in an image capture apparatus to execute a method comprising: applying, to an image captured using an auxiliary light source, correction processing for adding an effect of a virtual light source; and determining an amount of light to be emitted by the auxiliary light source for capturing the image to which the correction processing is applied, and determining a parameter used in the correction processing, wherein in the determining, the amount of light to be emitted and the parameter are determined based on a degree of shadows of an object to be captured using the auxiliary light source.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings. The following embodiments describe an exemplary application to a digital camera, which is an example of an image capture apparatus according to the present invention. The present invention can be embodied on any electronic device having a function of capturing images with an auxiliary light source emitting light (using the auxiliary light source); examples of such an electronic device include a mobile telephone device, a tablet terminal, a game console, and a personal computer. In the present specification, an "auxiliary light source" refers to a general "artificial light source", such as a flash apparatus and an LED light source, and is not necessarily equal to an "auxiliary light source" that is used in lighting as opposed to a "main light source".

(First Embodiment)

Figure 1:
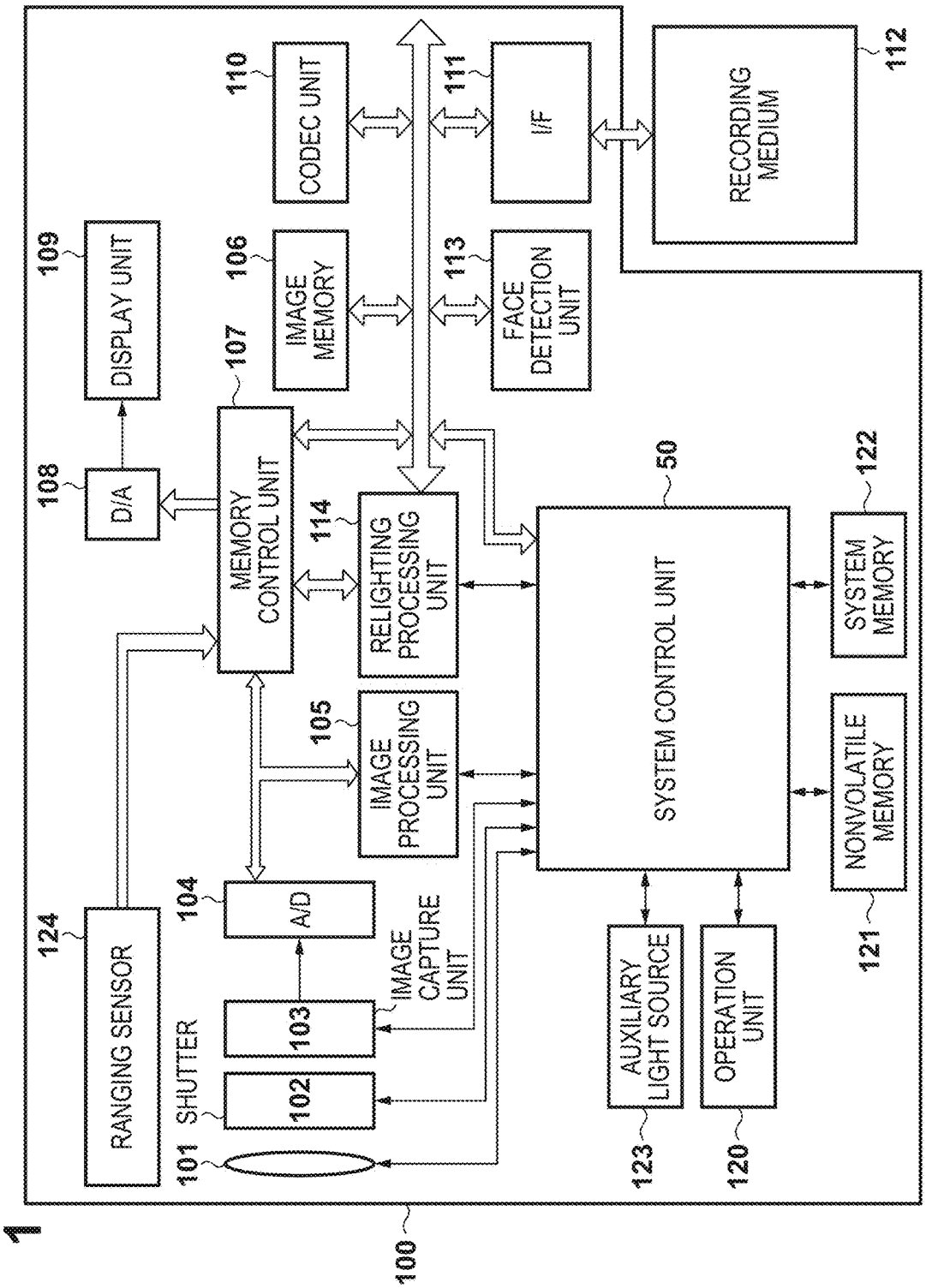
FIG. 1 is a block diagram showing an example of a functional configuration of a digital camera, which is an example of an image capture apparatus according to embodiments of the present invention.

FIG. 1 is a block diagram showing an example of a configuration of a digital camera 100 according to a first embodiment of the present invention.

In FIG. 1, a lens assembly 101 is a zoom lens assembly including a focus lens. A shutter 102 with a diaphragm function is arranged between the lens assembly 101 and an image capture unit 103. The image capture unit 103 has an image sensor that converts an optical image formed on an imaging surface by the lens assembly 101 into an electrical signal on a pixel-by-pixel basis; a typical example of such an image sensor is a CCD/CMOS image sensor. An A/D converter 104 converts an analog signal output from the image capture unit 103 into a digital signal (image data).

An image processing unit 105 applies, to image data output from the A/D converter 104, various types of image processing including color interpolation (demosaicing), white balance adjustment, γ correction, edge enhancement, noise reduction, color correction, etc. An image memory 106 temporarily stores image data. A memory control unit 107 controls reading and writing associated with the image memory 106. A D/A converter 108 converts image data into an analog signal. A display unit 109 has a display apparatus, such as an LCD and an organic EL display, and displays, among others, various types of GUIs, live-view images, and images that have been read out from a recording medium 112 and reproduced. A codec unit 110 encodes image data stored in the image memory 106 for the purpose of recording, external output, and the like, and also decodes encoded image data contained in an image file for the purpose of display and the like.

An interface (I/F) 111 mechanically and electrically connects the attachable/removable recording medium 112, which may be a semiconductor memory card and a card-shaped hard disk, to the digital camera 100. A system control unit 50 may be a programmable processor, such as a CPU and an MPU. The system control unit 50 realizes a function of the digital camera 100 by controlling a necessary block and circuit through the execution of a program recorded in, for example, a nonvolatile memory 121 and a built-in nonvolatile memory.

A relighting processing unit 114 applies relighting processing to a captured image. The relighting processing is correction processing for correcting brightness by lighting up an object in the image with light from a virtual light source. The relighting processing unit 114 may be realized by a combination of a microprocessor and software. It may also be realized by hardware, such as an application specific integrated circuit (ASIC) and a programmable logic device (PLD). Examples of a PLD include a field-programmable gate array (FPGA) and a programmable logic array (PLA).

It should be noted that the relighting processing can be applied to the following images.

Images captured in a state where the execution of the relighting processing is designated Images for which the execution of the relighting processing has been instructed via a menu screen and the like, and which have already been recorded in, for example, the recording medium 112

It will be assumed that, when the relighting processing requires information pertaining to the time of image capture, such information is read out from the nonvolatile memory 121 or a system memory 122, or is obtained from an image file header and the like.

A face detection unit 113 detects face regions included in a captured image, and obtains face information, such as a location, size, and degree of reliability, of each face region detected. It should be noted that the face detection unit 113 can detect face regions using any method, e.g., a method based on learning, typically neural networks, and a method that discovers such characteristic portions as the eyes, nose, and mouth from an image region using template matching, and that assumes the discovered portions as a face if they have a high degree of similarly.

Input devices, such as buttons and switches, used by a user for inputting various types of instructions to the digital camera 100 are collectively described in an operation unit 120. In a case where the display unit 109 is a touch display, a touchscreen is included in the operation unit 120. In addition, an input device for inputting an instruction in a contactless manner using sound, eye tracking, and the like may be included in the operation unit 120.

The nonvolatile memory 121 may be an electrically erasable and recordable memory, such as an EEPROM. Various types of setting values and GUI data are recorded in the nonvolatile memory 121; in a case where the system control unit 50 is an MPU or a CPU, a program executed by the system control unit 50 is also recorded therein.

The system memory 122 is used to deploy a constant and a variable for an operation performed by the system control unit 50, a program that has been read out from the nonvolatile memory 121, and the like.

An auxiliary light source 123 is typically a flash light apparatus, such as a flash, but may also be a continuously-lit LED or a similar light source. The auxiliary light source 123 need not be built in the digital camera 100 as long as the digital camera 100 can control the amount of light emitted thereby. Furthermore, a built-in auxiliary light source and an external auxiliary light source may be used in combination. A ranging sensor 124 measures a distance to an object, and generates a range image in which pixel values indicate distance information.

A description is now given of the operations performed by the digital camera 100 at the time of image capture.

For example, the image capture unit 103 causes the image sensor to photoelectrically convert an object image that is formed on the imaging surface by the lens assembly 101 while the shutter 102 is open, and outputs the resultant object image as an analog image signal to the A/D converter 104. The A/D converter 104 converts the analog image signal output from the image capture unit 103 into a digital image signal (image data), and outputs the digital image signal to the image processing unit 105.

The image processing unit 105 applies, to image data from the A/D converter 104 or image data from the memory control unit 107, various types of image processing including color interpolation (demosaicing), γ correction, edge enhancement, noise reduction, color correction, etc.

The image processing unit 105 also executes predetermined computation processing related to luminance, contrast, and the like using image data obtained through image capture, and the system control unit 50 performs ranging control and exposure control based on the obtained computation result. As such, the digital camera 100 according to the present embodiment executes through-the-lens (TTL) autofocus (AF) processing and TTL automatic exposure (AE) processing. The image processing unit 105 also performs automatic white balance (AWB) adjustment using image data obtained through image capture.

Image data output from the image processing unit 105 is written to the image memory 106 via the memory control unit 107. The image memory 106 stores image data output from the image capture unit 103, and image data to be displayed on the display unit 109.

The D/A converter 108 converts data that is stored in the image memory 106 for image display into an analog signal, and feeds the analog signal to the display unit 109. The display unit 109 causes the display apparatus, which may be an LCD, to perform display in accordance with the analog signal from the D/A converter 108.

The codec unit 110 encodes image data recorded in the image memory 106 based on the JPEG standard, the MPEG standard, etc. The system control unit 50 creates an image file by appending a preset header and the like to the encoded image data, and records the image file into the recording medium 112 via the interface 111.

It should be noted that digital cameras of today generally capture moving images in an image capture standby state, and cause the display unit 109 to function as an electronic viewfinder (EVF) by displaying the captured moving images continuously on the display unit 109. In this case, the shutter 102 is in an open state, and image capture is performed, for example, at 30 frames per second using a so-called electronic shutter of the image capture unit 103.

When a shutter button included in the operation unit 120 is pressed halfway down, the aforementioned AF control and AE control are performed; when the shutter button is pressed all the way down, a still image is captured for recording (main image capture), and the captured still image is recorded into the recording medium 112. When an instruction for capturing moving images is issued via a moving image capture button and the like, recording of moving images into the recording medium 112 is started.

(Image Processing Unit)

Figure 2:
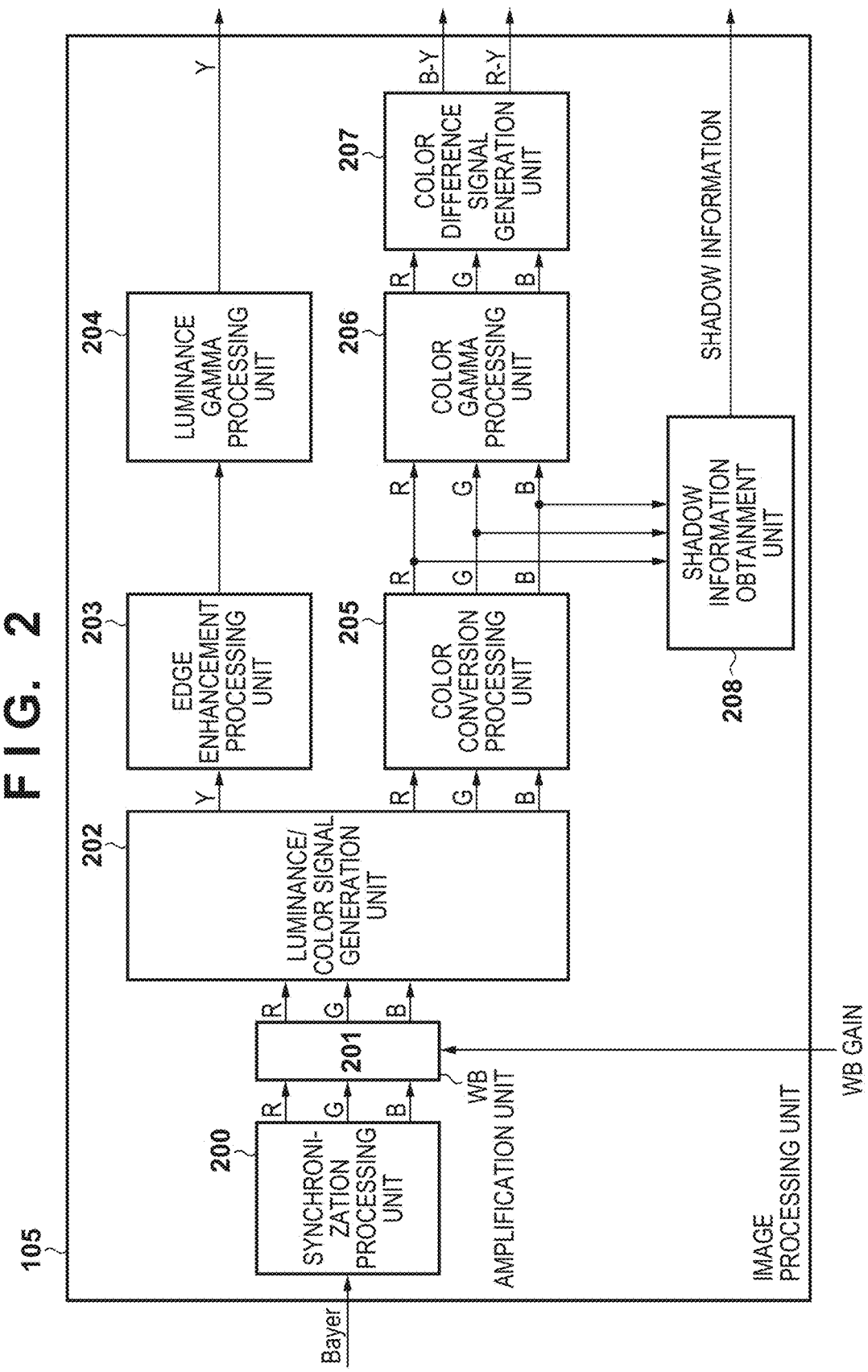
FIG. 2 is a block diagram showing an example of a functional configuration of an image processing unit shown in FIG. 1.

FIG. 2 is a block diagram showing an example of a functional configuration of the image processing unit 105.

Image data output from the A/D converter 104 shown in FIG. 1 is input to a synchronization processing unit 200. Image data has values that each correspond to one of color components constituting a color filter provided to the image sensor. In a case where an ordinary primary color filter with a Bayer array is used, image data is composed of data of R pixels, G pixels, and B pixels. The synchronization processing unit 200 applies synchronization processing (also referred to as demosaicing processing) to such image data so as to compensate for color components that are not included in each pixel, thereby generating image data in which each pixel has R, G, and B components. Hereinafter, R, G, and B components will be referred to as color signals.

A WB amplification unit 201 adjusts white balance by applying a gain to the color signals R, G, B of each pixel based on a white balance gain value calculated by the system control unit 50.

After white balance of the image data has been adjusted, the image data is input from the WB amplification unit 201 to a luminance/color signal generation unit 202. The luminance/color signal generation unit 202 generates a luminance signal Y from RGB components of the image data, and outputs the luminance signal Y to an edge enhancement processing unit 203. The luminance/color signal generation unit 202 also outputs the color signals R, G, B to a color conversion processing unit 205.

The edge enhancement processing unit 203 applies edge enhancement processing to the luminance signal Y, and outputs the resultant luminance signal Y to a luminance gamma processing unit 204. The luminance gamma processing unit 204 applies gamma correction to the luminance signal Y, and outputs the corrected luminance signal Y to the image memory 106 via the memory control unit 107.

The color conversion processing unit 205 converts the color signals R, G, B to have desired color balance through matrix computation and the like, and outputs the resultant color signals R, G, B to a color gamma processing unit 206 and a shadow information obtainment unit 208. The color gamma processing unit 206 applies gamma correction to the color signals R, G, B, and outputs the corrected color signals R, G, B to a color difference signal generation unit 207. The color difference signal generation unit 207 generates color difference signals R-Y (V or Cr), B-Y (U or Cb) from the gamma-corrected color signals R, G, B through, for example, RGB-YUV conversion. The color difference signal generation unit 207 outputs the color difference signals to the image memory 106 via the memory control unit 107.

The luminance signal Y and the color signals R-Y, B-Y output to the image memory 106 are encoded by the codec unit 110, and then recorded into the recording medium 112 or externally output by the system control unit 50.

The shadow information obtainment unit 208 obtains, from the color signals R, G, B output from the color conversion processing unit 205, information (shadow information) for analyzing the state of shadows cast by an environmental light source on an object, and outputs the obtained information to the image memory 106 via the memory control unit 107.

In the present embodiment, average luminance information of the object and luminance histogram information of a face region are obtained as the shadow information.

(Relighting Processing)

Figure 3:
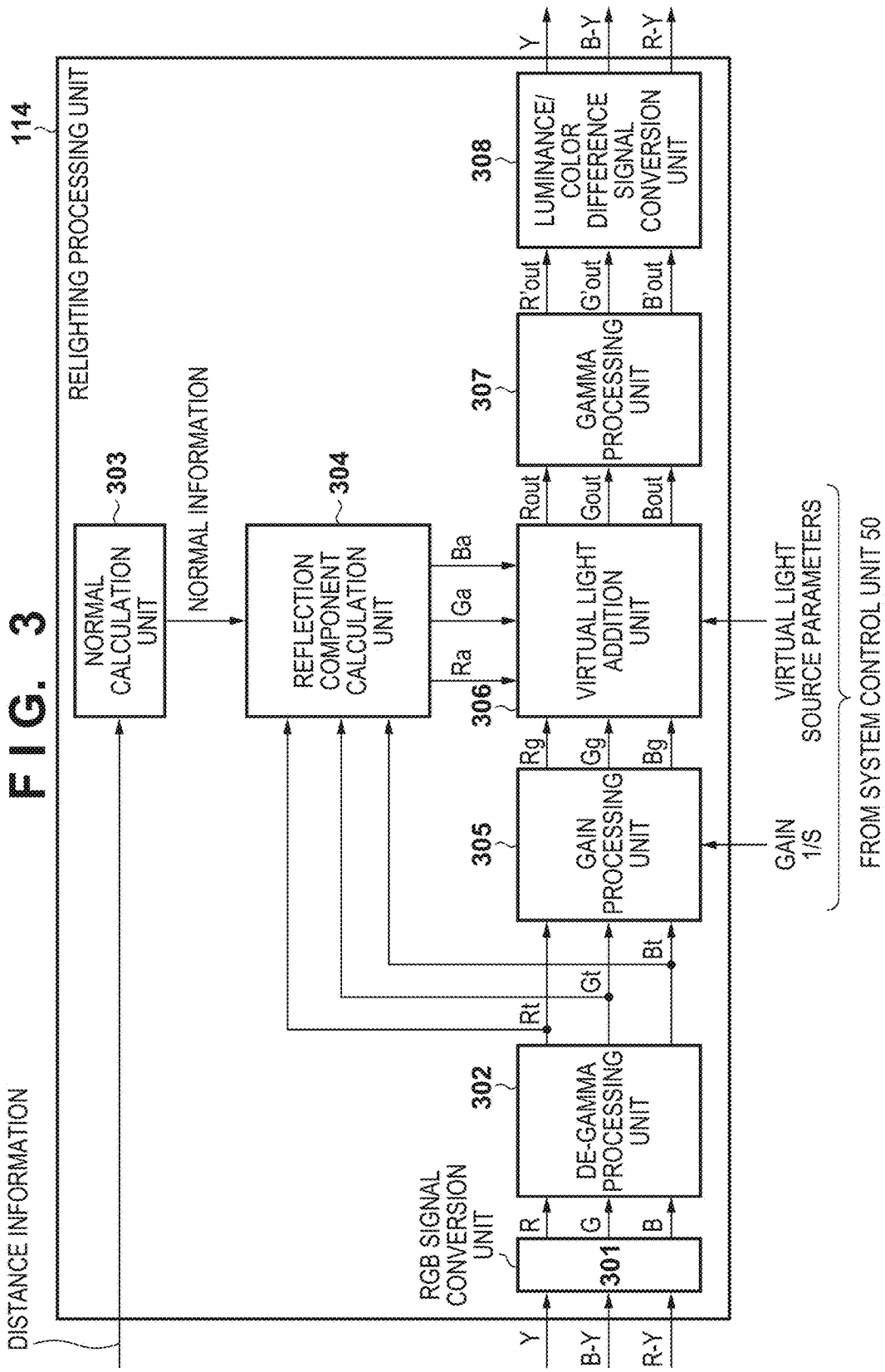
FIG. 3 is a block diagram showing an example of a functional configuration of a relighting processing unit shown in FIG. 1.

The configuration of and operations performed by the relighting processing unit 114 will now be described with reference to FIG. 3.

When the relighting processing is necessary (e.g., when the execution of the processing is selected by a user operation), the system control unit 50 inputs luminance and color difference signals output from the image processing unit 105 to the relighting processing unit 114 so as to execute relighting processing using a virtual light source.

An RGB signal conversion unit 301 converts the input luminance signal (Y) and color difference signals (B-Y, R-Y) into color signals (R, G, B), and outputs the color signals to a de-gamma processing unit 302. The de-gamma processing unit 302 applies de-gamma processing (the inverse of gamma correction processing applied by the luminance gamma processing unit 204 and the color gamma processing unit 206) to the color signals R, G, B. The de-gamma processing unit 302 outputs color signals Rt, Gt, Bt yielded from the de-gamma processing to a reflection component calculation unit 304 and a gain processing unit 305.

A normal calculation unit 303 calculates normals to a surface of an object from a range image output from the ranging sensor 124, and outputs information of the normals. The reflection component calculation unit 304 calculates, from the color signals Rt, Gt, Bt output from the de-gamma processing unit 302, color signals Ra, Ga, Ba representing components of virtual light that have been reflected by the object, and outputs the color signals Ra, Ga, Ba to a virtual light addition unit 306. The gain processing unit 305 applies a gain to the color signals Rt, Gt, Bt output from the de-gamma processing unit 302, and outputs color signals Rg, Gg, Bg yielded from the gain application to the virtual light addition unit 306. The virtual light addition unit 306 adds the relighting effect brought about by the virtual light source to image signals (color signals Rg, Gg, Bg) using the reflection components (color signals Ra, Ga, Ba), and outputs resultant color signals Rout, Gout, Bout.

A gamma processing unit 307 applies gamma correction to the color signals Rout, Gout, Bout yielded from the addition of the relighting effect, and outputs resultant color signals R'out, G'out, B'out. A luminance/color difference signal conversion unit 308 converts the color signals R'out, G'out, B'out into YUV format, and outputs a luminance signal Y and color different signals B-Y, R-Y representing an image yielded from the relighting processing.

The operations performed by the relighting processing unit 114 will now be described in detail.

The relighting processing unit 114 obtains, via the system control unit 50, luminance and color difference signals Y, B-Y, R-Y that have been output from the image processing unit 105 and recorded in the image memory 106. The RGB signal conversion unit 301 converts the input luminance and color difference signals Y, B-Y, R-Y into color signals R, G, B, and outputs the color signals R, G, B to the de-gamma processing unit 302.

The de-gamma processing unit 302 applies, to the color signals R, G, B, characteristics that are the inverse of gamma characteristics applied by the luminance gamma processing unit 204 and the color gamma processing unit 206 of the image processing unit 105, thereby converting the color signals R, G, B into color signals Rt, Gt, Bt corresponding to linear input/output characteristics. The de-gamma processing unit 302 outputs the color signals Rt, Gt, Bt yielded from the conversion to the reflection component calculation unit 304 and the gain processing unit 305.

Meanwhile, the normal calculation unit 303 calculates a normal map from a range image obtained from the ranging sensor 124. As stated earlier, a range image is information in which each pixel indicates a distance to an object at its position. There is no particular limit on a method of generating a normal map from a range image, and any known method may be used; the following describes a specific example of a generation method with reference to FIG. 4.

Figure 4:
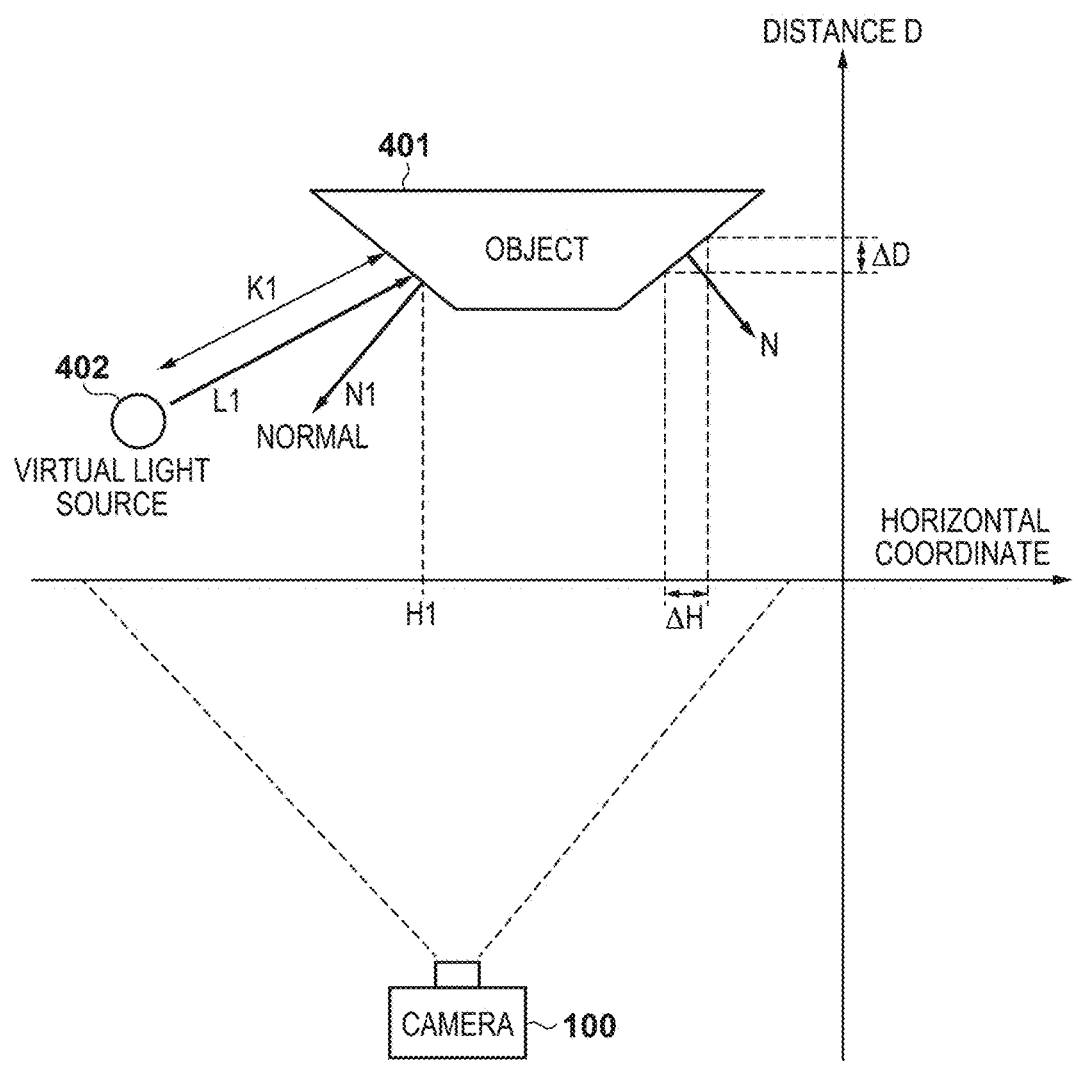
FIG. 4 is a diagram for describing an example of a method of generating a normal map from a range image in the embodiments.

FIG. 4 shows an example of a relationship between the camera and an object at the time of image capture as viewed from directly above. Here, horizontal coordinates are set along a direction parallel to an imaging surface, and distance coordinates are set along a direction parallel to an optical axis. In this case, gradient information can be calculated from a difference $\Delta D$ between distances (depths) D corresponding to a difference $\Delta H$ along a horizontal direction within a captured image of an object 401, and a normal vector N of a surface can be calculated from the gradient information. Normal vectors N corresponding to pixels in the captured image can be calculated using the values of pixels constituting a range image and the principle shown in FIG. 4. The normal calculation unit 303 outputs information of the normal vectors N corresponding to the pixels in the captured image as a normal map to the reflection component calculation unit 304.

The reflection component calculation unit 304 calculates reflection components, on the surface of the object, of virtual light set at a predetermined position based on a distance K between the virtual light source and the object, the information of a normal vector N, and virtual light source parameters (determined by the system control unit 50 in later-described processing). Specifically, reflection components at a coordinate position corresponding to the captured image are calculated such that they are inversely proportional to the square of a distance K between the virtual light source and the surface of the object, and they are proportional to the inner product of a normal vector N of the object and a direction vector L of the light source.

Below, processing for calculating reflection components of virtual light will be described again with reference to FIG. 4. It will be assumed that a virtual light source 402 is arranged as illustrated in FIG. 4. In this case, reflection components of virtual light at a pixel corresponding to a horizontal coordinate H1 within an image captured by the camera 100 are proportional to the inner product of a normal vector N1 and a direction vector L1 of the virtual light source at the coordinate H1, and are inversely proportional to a distance K1 between the virtual light source 402 and the object 401. It should be noted that a vertical coordinate is omitted here to simplify the explanation.

Based on the foregoing relationship, color signals Ra, Ga, Ba representing the reflection components of the virtual light on the object can be expressed by the following expressions.

$$Ra = \alpha \times (-L \cdot N)/K^2 \times Rw \times Rt$$

$$Ga = \alpha \times (-L \cdot N)/K^2 \times Gt$$

$$Ba = \alpha \times (-L \cdot N)/K^2 \times Bw \times Bt$$

Here, $\alpha$ denotes the intensity of the virtual light source, L denotes a three-dimensional direction vector of the virtual light source, N denotes a three-dimensional normal vector of the object, and K denotes a distance between the virtual light source and the object. Furthermore, Rt, Gt, Bt denote the values of color signals output from the de-gamma processing unit 302, and Rw, Bw denote parameters for controlling the color of the light source.

As will be described later with reference to FIG. 5, in the present embodiment, control parameters Rw, Bw are set to coordinate the color of the virtual light source with the color of the environmental light source. The control parameters Rw, Bw can be calculated from values of color signals in a state where the virtual light source is not emitting light, and values of color signals in a state where the virtual light source is emitting light, as follows.

$$Rw = (R \text{ under no light emission}/G \text{ under no light emission})/(Rt/Gt)$$

$$Bw = (B \text{ under no light emission}/G \text{ under no light emission})/(Bt/Gt)$$

The reflection component calculation unit 304 outputs the color signals Ra, Ga, Ba thus calculated, which are equivalent to the reflection components of the virtual light source, to the virtual light addition unit 306.

Meanwhile, the gain processing unit 305 applies a gain 1/S designated by the system control unit 50 to the color signals Rt, Gt, Bt input from the de-gamma processing unit 302 as indicated by the following expressions, and outputs color signals Rg, Gg, Bg yielded from the gain adjustment.

$$Rg = Rt/S$$

$$Gg = Gt/S$$

$$Bg = Bt/S$$

Here, 1/S is a gain that reduces the brightness of a portion lit up by the light of the auxiliary light source 123 (auxiliary light). The effect of the gain and a method of determining the gain will be described later.

The virtual light addition unit 306 adds the reflection components of the virtual light (color signals Ra, Ga, Ba) to the color signals Rg, Gg, Bg for an object region lit up by the auxiliary light, thereby obtaining color signals Rout, Gout, Bout that reflect the virtual light.

Rout=Rg+Ra

Gout=Gg+Ga

Bout=Bg+Ba

It should be noted that an object region that is not lit up by the auxiliary light is treated as a region including no reflection component of the virtual light.

The color signals Rout, Gout, Bout output from the virtual light addition unit 306 are input to the gamma processing unit 307. The gamma processing unit 307 applies gamma correction to the input color signals, and outputs the resultant color signals R'out, G'out, B'out. The luminance/color difference signal conversion unit 308 converts the gamma-corrected color signals R'out, G'out, B'out into a YUV format, and outputs a luminance signal Y and color difference signals R-Y, B-Y as image signals yielded from the relighting processing.

The system control unit 50 writes the luminance signal and the color difference signals output from the relighting processing unit 114 to the image memory 106 by controlling the memory control unit 107. The system control unit 50 then encodes the luminance and color difference signals in the image memory 106 by controlling the codec unit 110, and records the encoded luminance and color difference signals into the recording medium 112 or externally outputs them via the I/F 111.

(Operation to Determine Relighting Processing Parameters)

A description is now given of an operation performed by the system control unit 50 to determine relighting processing parameters (the virtual light source parameters, the gain, and the amount of light to be emitted by the auxiliary light source 123) used in the above-described relighting processing unit 114. In the present embodiment, the system control unit 50 determines the relighting processing parameters based on the shadow information output from the image processing unit 105.

The system control unit 50 performs a preliminary image capture operation prior to main image capture. A user operation of the operation unit 120 may serve as a trigger to perform the preliminary image capture, or the preliminary image capture may be automatically performed as image capture for generating a preview image. The preliminary image capture can be performed through processing that is similar to processing for live-view image capture and main image capture, except that the auxiliary light source 123 does not emit light (is not used) during the preliminary image capture. The image processing unit 105 applies the above-described processing to an image obtained through the preliminary image capture, and the resultant image is stored into the image memory 106 via the memory control unit 107.

Figure 5:
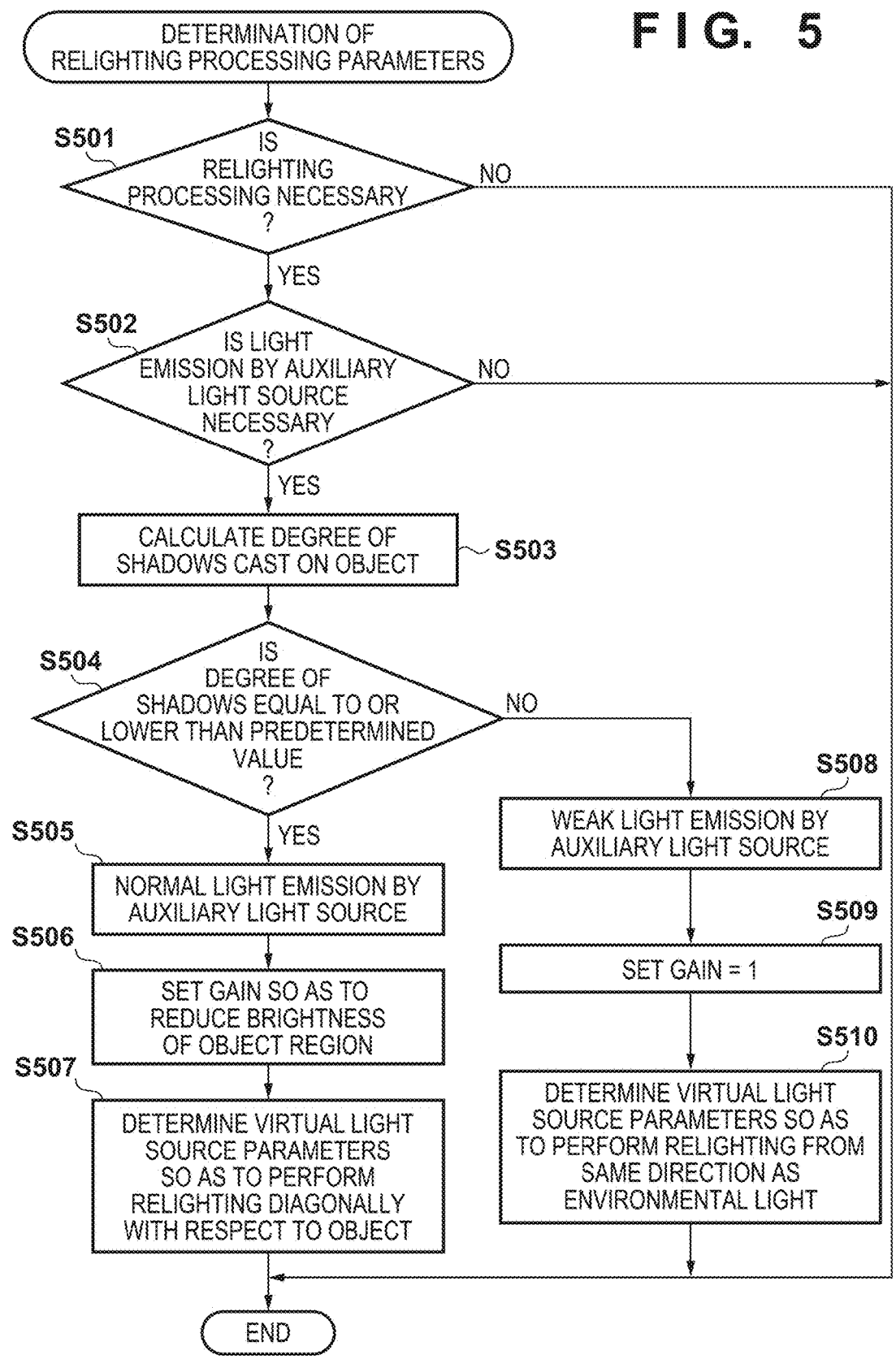
FIG. 5 is a flowchart for describing processing for determining relighting parameters in a first embodiment.

FIG. 5 is a flowchart showing an operation performed by the system control unit 50 at the time of preliminary image capture (no light emission) preceding main image capture. In line with the flowchart of FIG. 5, the following describes an operation performed by the system control unit 50 to determine the relighting processing parameters based on the state of shadows.

In step S501, the system control unit 50 determines whether the relighting processing needs to be executed. This determination can be made based on, for example, whether the execution of the relighting processing, or the execution of an operation that accompanies the relighting processing, has been set by a user operation of the operation unit 120. The system control unit 50 proceeds to step S502 if the execution of the relighting processing is determined to be necessary, and ends the processing if the execution of the relighting processing is determined to be unnecessary.

In step S502, the system control unit 50 analyzes the brightness of an image yielded from the preliminary image capture. Specifically, the system control unit 50 analyzes the average luminance information of an object, which is included in the shadow information output from the image processing unit 105 to the image memory 106. If the average luminance information of the object indicates a shortage in the brightness of the object (the brightness of the object is lower than correct brightness that has been preset), the system control unit 50 determines that light emission by the auxiliary light source 123 (auxiliary light) is necessary. The system control unit 50 proceeds to step S503 if light emission by the auxiliary light source 123 is determined to be necessary, and ends the processing if light emission by the auxiliary light source 123 is determined to be unnecessary.

In step S503, the system control unit 50 analyzes the luminance histogram information of a face region, which is included in the shadow information output from the image processing unit 105 to the image memory 106, and calculates a degree of shadows cast on the object. A degree of shadows is a value indicating a degree of spreading of the distribution of a bright portion and a dark portion, and a specific description thereof will now be given with reference to FIGS. 6A to 6E.

Figure 6A:
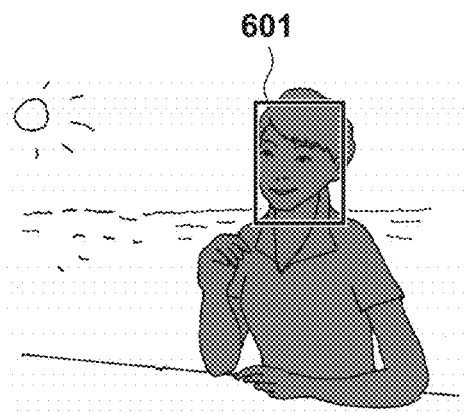
FIGS. 6A to 6E are diagrams for describing an example of a method of determining a degree of shadows in the first embodiment.
Figure 6B:
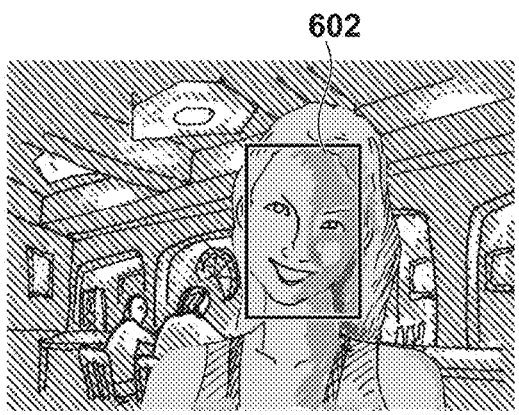
Figure 6C:
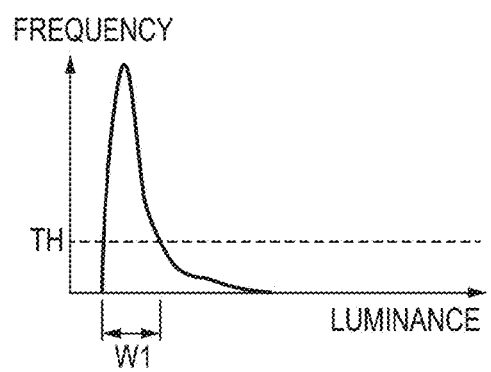
Figure 6D:
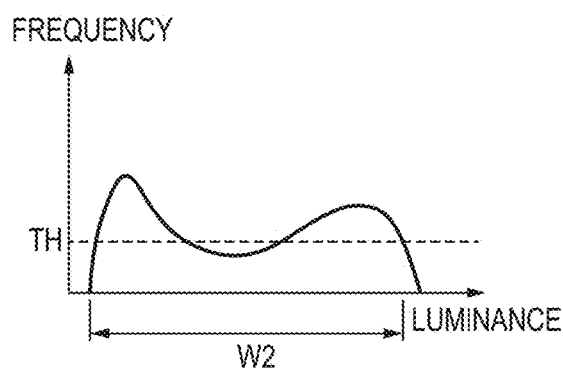

FIGS. 6A and 6B show examples of images obtained through preliminary image capture, FIG. 6C shows a luminance histogram of a face region 601 in FIG. 6A, and FIG. 6D shows a luminance histogram of a face region 602. It should be noted that the system control unit 50 extracts pixels having the hues and saturations of preset skin colors from among pixels included in a face region, and generates a luminance histogram for the extracted pixels.

The system control unit 50 calculates a degree of shadows based on the number of tones with luminances corresponding to a frequency of a predetermined threshold TH or higher in a luminance histogram. Although there is no limit on a specific calculation method, the system control unit 50 performs calculation such that the more widespread the luminances corresponding to a frequency of the threshold TH or higher, the higher the degree of shadows. More specifically, it performs calculation such that the larger the difference between the lowest luminance and the highest luminance corresponding to a frequency of the threshold TH or higher, the higher the degree of shadows. In this way, the degree of shadows is high when an object region significantly exhibits bright and dark (shaded) portions, and low when the object region is bright or dark as a whole. A relationship between a specific value of the degree of shadows and a magnitude of the difference between the lowest luminance and the highest luminance corresponding to a frequency of the threshold TH or higher can be determined as appropriate.

Specifically, in FIG. 6A, the entire object is in the shade as it was backlit during image capture; accordingly, in the luminance histogram for the face region 601 (FIG. 6C), luminances corresponding to a frequency of the threshold TH or higher are focused in a low-luminance range, and the spreading W1 of such luminances is small (narrow). On the other hand, in FIG. 6B, image capture was performed indoors, and the object includes both a portion lit up by illumination and a shaded portion; accordingly, in the luminance histogram for the face region 602 (FIG. 6D), the spreading W2 of luminances corresponding to a frequency of the threshold TH or higher is large (wide). Therefore, the degree of shadows of the face region 602 is higher than the degree of shadows of the face region 601.

Returning to FIG. 5, in step S504, the system control unit 50 determines whether the degree of shadows calculated in step S503 is low (equal to or lower than a predetermined value), and proceeds to step S505 if the degree of shadows is equal to or lower than the predetermined value, and to step S508 if the degree of shadows exceeds the predetermined value.

In steps S505 and S508, the system control unit 50 determines the amount of light to be emitted by the auxiliary light source at the time of main image capture, which is performed after the preliminary image capture. Specifically, if the degree of shadows of the object is equal to or lower than the predetermined value (step S505), the system control unit 50 determines a normal light emission amount that achieves correct exposure upon emission of light by the auxiliary light source. This is because, when the degree of shadows is low, even if the shadows are reduced in intensity due to emission of light by the auxiliary light source, the influence thereof is considered small.

On the other hand, if the degree of shadows exceeds the predetermined value (step S508), the system control unit 50 determines that the auxiliary light source should emit a smaller amount of light (weaker light) than normal. This is because, when the degree of shadows is not low, if the shadows cast by environmental light on the object are weakened by emission of light by the auxiliary light source, the influence thereof is considered large. For this reason, the auxiliary light source emits weaker light than normal so as to suppress the influence on the shadows cast by the environmental light. A shortage in the amount of exposure caused by the emission of weaker light than normal is compensated for by the relighting processing using the virtual light source.

In steps S506, S507, S508, and S509, the system control unit 50 determines a gain and virtual light source parameters.

If the degree of shadows of the object is equal to or lower than the predetermined value, the system control unit 50 sets the gain (1/S) used in the gain processing unit 305 of the relighting processing unit 114 (FIG. 3) so as to reduce the brightness of the object region in step S506. Here, the relationship S>1 holds, and the value of S can be set so as to reduce the brightness of the object region to a value that is equivalent or similar to the brightness achieved when light is not emitted by the auxiliary light source.

Figure 7A:
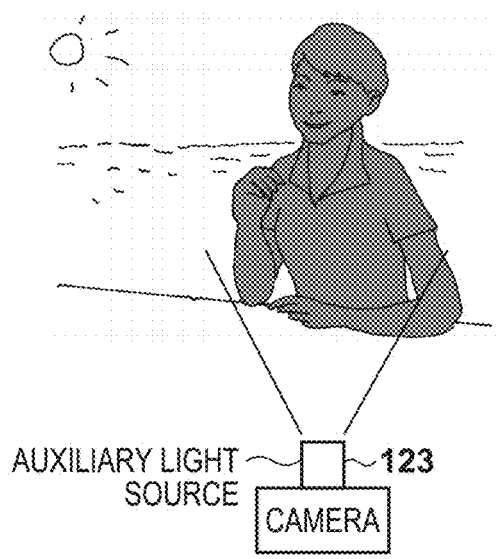
FIGS. 7A to 7D are diagrams for describing a specific example of relighting processing in the first embodiment.
Figure 7B:
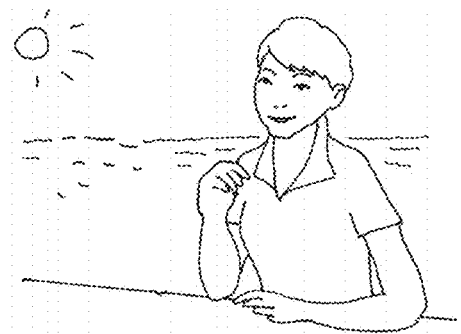

The foregoing will be illustrated below with reference to examples of FIGS. 7A to 7D. FIG. 7A shows an example of an image captured without the auxiliary light source emitting light in a backlit scene; in this example, the degree of shadows of an object region is equal to or lower than the predetermined value. FIG. 7B shows an example of an image captured with the auxiliary light source emitting light of the normal light emission amount (a light emission amount that achieves correct exposure for the object region) in the same scene as FIG. 7A. Applying the above-described gain (1/S) to the image of FIG. 7B results in the state of FIG. 7C that is close in brightness to FIG. 7A in which the auxiliary light source does not emit light.

In step S507, the system control unit 50 determines the following as the virtual light source parameters: the intensity α of the virtual light source, which is used in generating the reflection components of the virtual light source (Ra, Ga, Ba), and the position of the virtual light source.

The intensity α of the virtual light source is equivalent to a luminance value of virtual light at the position of the virtual light source. The intensity α of the virtual light source can be determined such that, upon arrival at a surface of the object, the value thereof compensates for the luminance reduced by the gain processing unit 305.

In the present case, the system control unit 50 can determine the intensity α of the virtual light source such that the luminance α' at a position distanced from the virtual light source by an object distance K satisfies the following relationship.

$$\alpha' = 1 - (1/S)$$

It will be assumed that a distance K between a main object and the virtual light source is preset in consideration of a light source model so as to, for example, light up a main object region with uniform brightness.

Figure 7C:
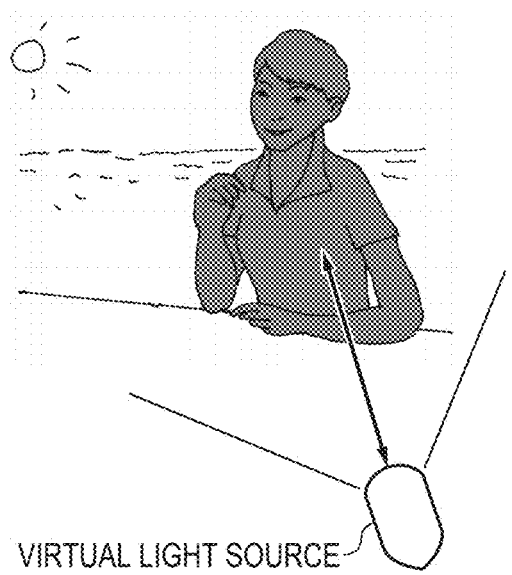
Figure 7D:
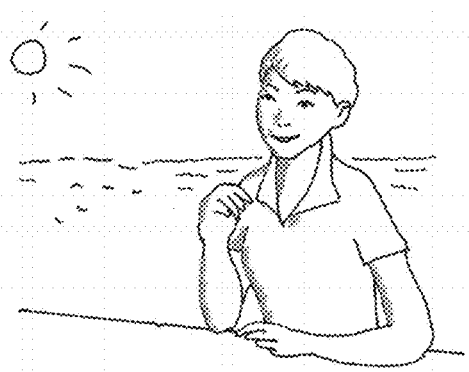

The system control unit 50 also sets the position of the virtual light source such that a direction thereof enables easy casting of shadows on the main object (person). For example, the position can be set such that the main object is lit up from a diagonal direction, e.g., from a direction of 45 degrees with respect to the horizontal direction, as shown in FIG. 7C. The angle by which the object is lit up may be set as an angle with respect to the optical axis, or may be set as an angle with respect to a normal to a front surface of the object in a case where the orientation can be identified, e.g., in a case where the object is a person.

In the above-described manner, the system control unit 50 determines the virtual light source parameters (intensity, position (angle and distance)) and the gain (1/S or S) of the gain processing unit 305, and sets them in the relighting processing unit 114. An image shown in FIG. 7D, which includes shadows, can be obtained by the relighting processing unit 114 executing the above-described relighting processing in accordance with these settings. As an image targeted for the relighting processing is captured with the auxiliary light source emitting light to achieve correct exposure for the object region (FIG. 7B), even if processing for brightening a portion that has been darkened by gain reduction is executed with the aid of virtual light, noise in the dark portion is not amplified.

On the other hand, if the degree of shadows of the object exceeds the predetermined value, in steps S509 and S510, the system control unit 50 determines a gain and virtual light source parameters for the relighting processing targeting an image that has been obtained through main image capture of an object on which shadows are cast by an environmental light source, such as an image shown in FIG. 6B.

First, in step S509, the system control unit 50 sets the gain used in the gain processing unit 305 (1/S) to 1, that is to say, S=1. It means that the brightness of the image obtained through the main image capture is not changed. It should be noted that, when 1/S=1, the gain processing unit 305 may apply a gain of 1 to the image, or may not perform gain application.

Next, in step S510, the system control unit 50 sets the intensity α of the virtual light source, which is used in generating the reflection components of the virtual light (color signals Ra, Ga, Ba), to the intensity that compensates for a shortage in the amount of exposure relative to correct exposure, the shortage being caused by emission of weak light by the auxiliary light source.

The system control unit 50 also determines the position of the virtual light source (the direction of emission of the virtual light) such that the virtual light lights up the object similarly to the environmental light. There is no limit on a method of estimating the position of the environmental light source (the direction of emission of the environmental light); for example, the position of the environmental light source can be estimated from the orientation of shadows cast on the main object.

Figure 9:
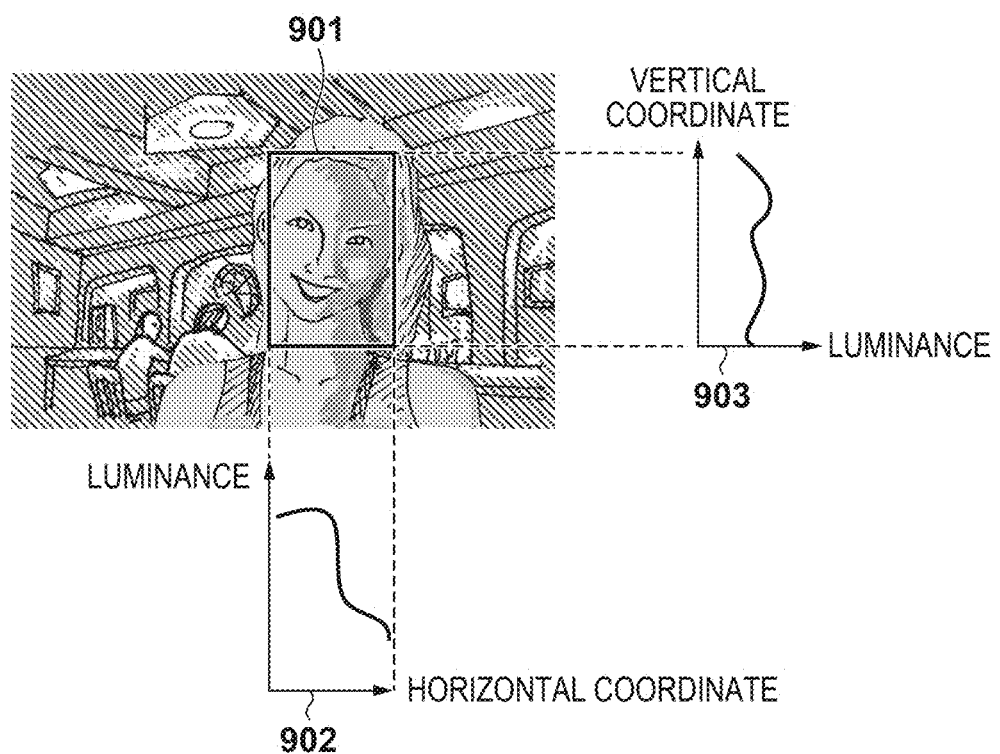
FIG. 9 is a diagram for describing a method of estimating the position of an environmental light source in the first embodiment.

The specifics of a method of estimating the position of the environmental light source will now be described with reference to an example shown in FIG. 9. In a case where the main object is a person, the system control unit 50 obtains, from a face region 901, average luminances in a skin-color portion along the horizontal and vertical directions. Then, based on an average luminance distribution 902 in a skin-color face region along the horizontal direction, the system control unit 50 determines which one of the left and right portions of the face is brighter, using the nose as the center. In the example of FIG. 9, the distribution indicates that the left portion is brighter. In this case, it can be estimated that the environmental light source is positioned to the left of the face. Similarly, based on an average luminance distribution 903 in the skin-color face region along the vertical direction, the system control unit 50 determines which one of the upper and lower portions of the face is brighter, using the center of the nose as a reference. In the example of FIG. 9, as there is no large difference between the upper and lower portions, it can be estimated that the height of the environmental light source is similar to the height of the nose.

In the above-described manner, the position of the environmental light source along the horizontal and vertical directions is estimated, and the virtual light source is set at a position that is distanced from the object by a distance K, along a direction similar to a direction along which the environmental light source is set with respect to the object.

A description is now given of the relighting processing that is executed in accordance with the settings of the above-described gain and virtual light source parameters with reference to FIGS. 8A to 8D.

Figure 8A:
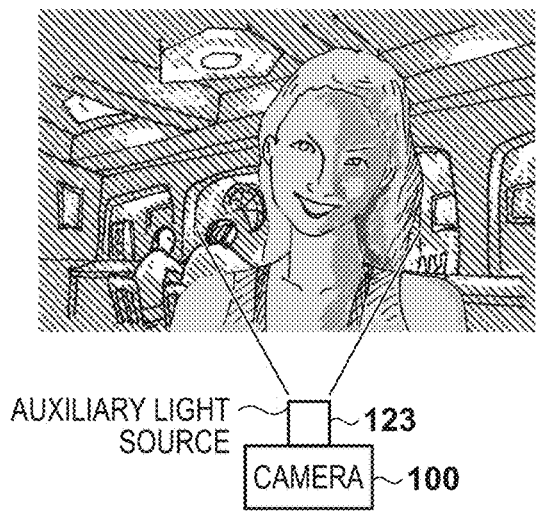
FIGS. 8A to 8D are diagrams for describing a specific example of the relighting processing in the first embodiment.
Figure 8B:
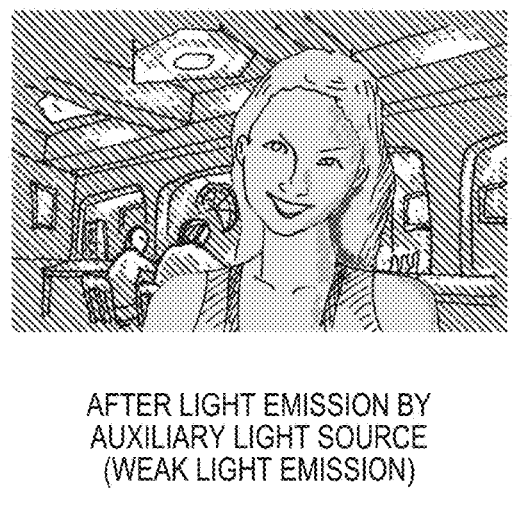

FIG. 8A shows an example of an image yielded from preliminary image capture without the auxiliary light source emitting light; in this example, the degree of shadows of an object region is equal to or higher than the predetermined value due to environmental light. FIG. 8B shows an example of an image captured with the auxiliary light source emitting an amount of light that is smaller than the normal light emission amount determined in step S508 (a light emission amount that achieves correct exposure for the object region) in the same scene as FIG. 8A. As the auxiliary light source emits somewhat weak light, shadows cast by the environmental light remain.

Figure 8C:
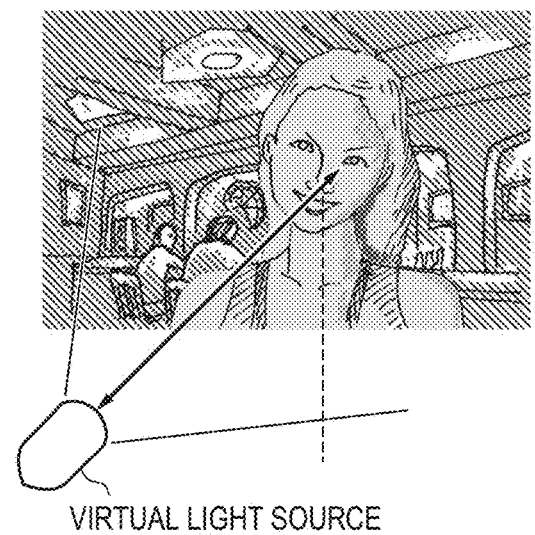
Figure 8D:
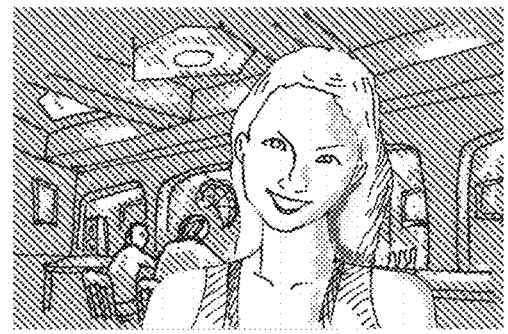

As the gain (1/S)=1 is set in step S509 as described above, relighting is applied to the image of FIG. 8B using the virtual light source. FIG. 8C schematically shows the relighting processing; the virtual light source is set along a direction similar to the direction of the environmental light source, as determined in step S510. The intensity α of the virtual light source is set so as to compensate for a shortage in the brightness of the object caused by emission of weak light by the auxiliary light source. FIG. 8D shows an image yielded from the relighting processing. In such a case where the degree of shadows cast by the environmental light on the object exceeds the predetermined value, the amount of light to be emitted by the auxiliary light source at the time of main image capture is made smaller than the normal light emission amount, so that the auxiliary light does not eliminate the shadows cast by the environmental light. By compensating for a shortage in the auxiliary light through the relighting processing, an image presenting an object with correct brightness and natural shadows can be obtained. The relighting processing can increase natural shadows, especially by setting the position of the virtual light source such that the virtual light lights up the object from a direction similar to the direction of the environmental light.

As described above, the present embodiment determines the amount of light to be emitted by the auxiliary light source at the time of main image capture, as well as the gain and virtual light source parameters used in the relighting processing, in accordance with a detected degree of shadows that are cast by the environmental light on an object in an image captured without using the auxiliary light source. Specifically, if the degree of shadows cast by the environmental light is low, an image obtained with the auxiliary light source emitting a normal amount of light is reduced in brightness, and then the relighting processing is executed. In this way, the relighting processing can add shadows to an object captured in, for example, a backlit scene without increasing noise in a dark portion. On the other hand, if the degree of shadows cast by the environmental light is not low, the relighting processing is applied to an image obtained with the auxiliary light source emitting a smaller amount of light than normal. In this way, an image presenting correct brightness and natural shadows can be obtained without the auxiliary light eliminating natural shadows cast by the environmental light.

In the present embodiment, the degree of shadows of the object (the intensity of shadows cast by the environmental light) is determined based on a luminance histogram of a characteristic region in the object. However, the degree of shadows is not limited to being determined using this method, and may be determined using any other method. For example, the state of shadows can be determined using brightness information of a scene of image capture and the result of determination of whether the scene is in a backlit state. Specifically, it can be determined that the degree of shadows is low if the scene is backlit or dark, and that the degree of shadows is not low if the scene is backlit but is not identified as a dark scene.

Also, the degree of shadows may be determined using shape information of the object. The shape information indicates a degree of complexity of the shape of the object, and can be obtained from, for example, a spatial frequency of the amplitude of distance information obtained from the ranging sensor 124. Specifically, if the spatial frequency of the amplitude of the distance information is determined to be high, the distance to the object changes in a complex manner, and thus it can be determined that the object has a complex shape with many recesses and projections on its surface; on the other hand, if the spatial frequency of the amplitude of the distance information is determined to be low, it can be determined that the object has a planar surface.

Figure 6E:

For example, in the case of an object with a complex shape, such as the kimono worn by the objects (people) in an image of FIG. 6E, extremely precise shape information (distance information) is required to add accurate shadows through relighting. Therefore, by setting the auxiliary light source to emit a somewhat small amount of light so that the auxiliary light does not eliminate the shadows that have been originally cast by the environmental light source, an image with an appropriate amount of exposure can be obtained while preserving natural shadows.

In the above-described present embodiment, if the degree of shadows of the object is determined to be low, the auxiliary light source emits a normal amount of light at the time of main image capture. However, the auxiliary light source is not limited to emitting a normal amount of light, and, for example, can emit a larger amount of light than normal (it should be noted that the amount of light emission shall not bring about blown-out highlights in a region that has been lit up).

By performing image capture so as to brighten, in advance, a portion that will be brightened through the relighting processing after gain reduction, amplification of noise in a dark portion by the relighting processing can be suppressed.

In the above description, if the degree of shadows of the object is not determined to be low, a smaller amount of light than normal is emitted at the time of main image capture, and exposure conditions are not changed. Alternatively, the exposure conditions may be changed so as to increase the amount of exposure, and the amount of light to be emitted by the auxiliary light source may be further reduced accordingly. This can alleviate the loss of shadows, which occurs even when the auxiliary light source emits weak light.

Although the present embodiment has described an example case in which a main object is a person (face) for ease of understanding and explanation, a main object is not limited to a person, and may be any detectable object.

(Second Embodiment)

A second embodiment of the present invention will now be described. In the first embodiment, the relighting processing parameters (the amount of light to be emitted by the auxiliary light source, the gain, and the virtual light source parameters) are determined in accordance with the degree of shadows cast by environmental light on an object. In the present embodiment, the degree of shadows cast by the auxiliary light is predicted, and the relighting processing parameters are determined in accordance with the result of prediction. In the present embodiment, the degree of shadows cast by the auxiliary light is estimated using distance information of an object.

The present embodiment can be implemented on a digital camera that is similar in configuration to the digital camera according to the first embodiment, and processing executed by the system control unit 50 to determine the relighting processing parameters differs in the present embodiment. Therefore, below, processing for determining the relighting processing parameters according to the present embodiment will be described, and a description of configurations and operations that are shared in common with the first embodiment will be omitted.

Figure 10:
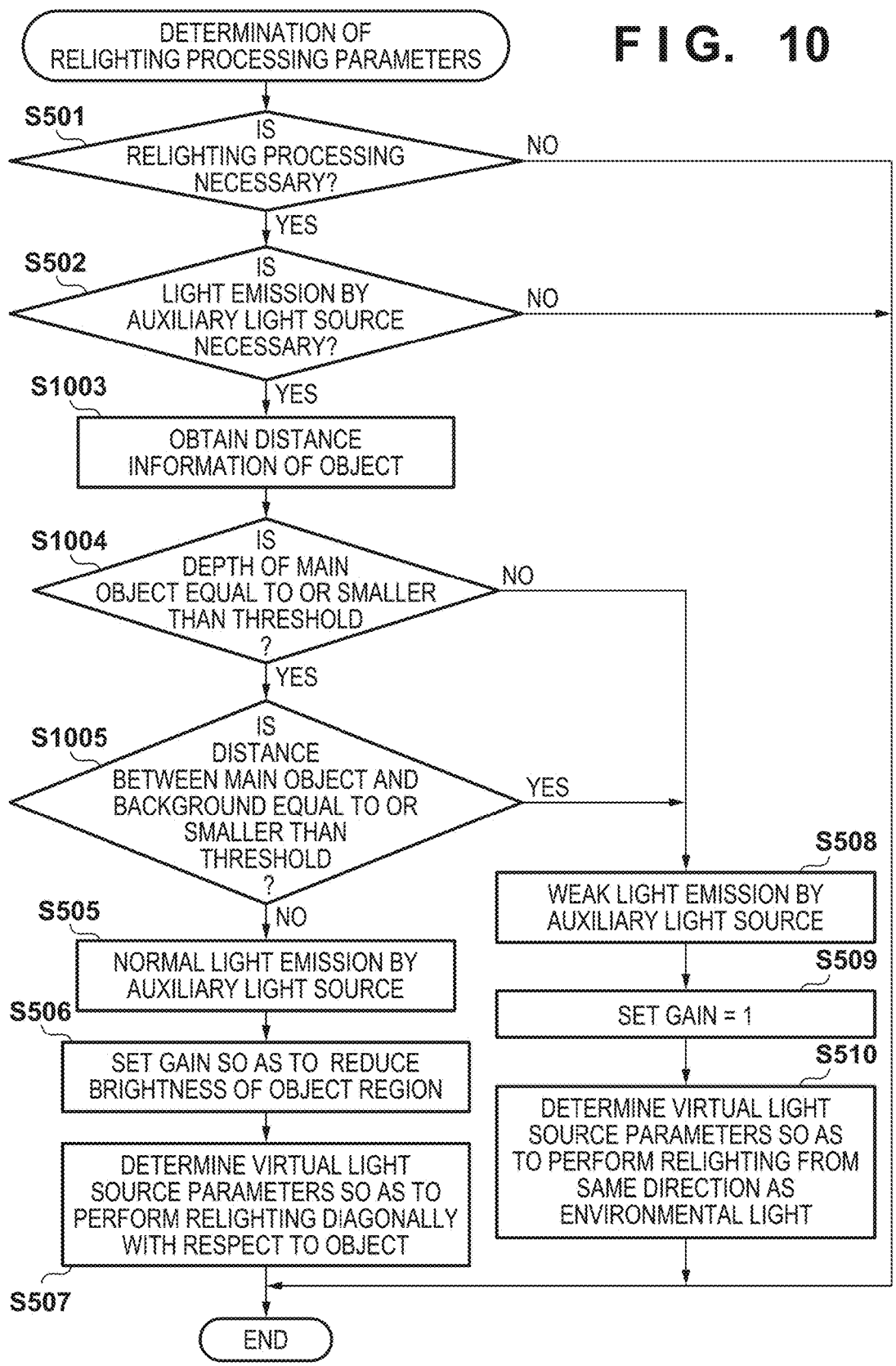
FIG. 10 is a flowchart for describing processing for determining relighting parameters in a second embodiment.

FIG. 10 is a flowchart showing an operation performed by the system control unit 50 at the time of preliminary image capture (no light emission) preceding main image capture, and steps therein that execute processes similar to the processes of the first embodiment are given the same reference numerals thereas. In line with the flowchart of FIG. 10, the following describes an operation performed by the system control unit 50 to determine the relighting processing parameters based on the state of shadows.

In steps S501 and S502, similarly to the first embodiment, the system control unit 50 determines whether the relighting processing needs to be executed (step S1001), and determines whether a current scene requires light emission by the auxiliary light source 123 if the relighting processing needs to be executed (step S1002).

In step S1003, the system control unit 50 analyzes a range image from the ranging sensor 124 (FIG. 1), and calculates the depth of a main object (a distance range over which the main object exists) and the distance between the main object and a background. This calculation will now be described with reference to FIGS. 11A to 11D.

Figure 11A:
FIGS. 11A to 11D are diagrams for describing a method of estimating a degree of shadows in the second embodiment.

Among FIGS. 11A to 11D, which show examples of captured objects, FIG. 11A pertains to an example in which a main object is a person. In this example, the person serving as the main object is extending her right hand toward the camera, that is to say, the object has a depth. The system control unit 50 calculates the distance between the front (hand) to the back (face) of the main object as depth information. Specifically, the system control unit 50 can cut out a main object region of the range image through known processing, and calculate a difference between the smallest value and the largest value of the distances to the object indicated by pixels within the main object region as depth information. Although FIG. 10B also pertains to an example in which a person is a main object, she is not extending her hand, and the depth of an object region thereof is small compared to the example of FIG. 10A.

Figure 11B:

A description is now given of a distance between a main object and a background. In the scenes of FIGS. 11A and 11B, there is a distance of a certain length or more (e.g., 5 m or more) between a main object (person) and a background. In contrast, FIG. 11C exemplarily shows an indoor scene where a wall stands immediately behind a person serving as a main object, that is to say, the distance between the main object and the background is small. In this case, the distance between a main object region and a background region can be calculated from, for example, a difference between the distance to a face portion 1101 of the main object and the distance to a region 1102 or 1103 that is located in an upper part of a screen and that is not included in the main object region.

In step S1003, the system control unit 50 thus calculates, as the distance information of the object, depth information of the main object and distance information of the main object and the background, and stores the distance information of the object into, for example, the system memory 122.

In step S1004, the system control unit 50 determines whether the depth of the main object calculated in step S1003 is equal to or smaller than a predetermined threshold, and proceeds to step S1005 if the depth is equal to or smaller than the threshold, and to step S508 if the depth is larger than the threshold.

In step S1005, the system control unit 50 determines whether the distance between the main object and the background is equal to or smaller than a predetermined threshold, and proceeds to step S508 if the distance is equal to or smaller than the threshold, and to step S505 if the distance is larger than the threshold.

As the processes executed in steps S505 to S510 are similar to those in the first embodiment, a detailed description thereof is omitted.

In the present embodiment, when the depth of the main object is larger than a threshold, or when the distance between the main object and the background is equal to or smaller than a threshold, the relighting processing is executed while leaving the shadows cast by the environmental light by causing the auxiliary light source to emit a smaller amount of light than normal. This is because, when the depth of the main object is larger than a threshold as shown in FIG. 11A, there will be variations in the effect of the auxiliary light within the main object region. That is to say, within a region of the same person, a location close to the camera is strongly irradiated with the auxiliary light, whereas a location far from the camera is weakly irradiated with the auxiliary light. Differences in luminance, if derived from the auxiliary light, do not represent natural shadows and leave an unnatural ambience even with the addition of shadows through relighting. For this reason, when the depth of the main object is equal to or larger than a threshold, the auxiliary light source emits somewhat weak light, and shadows cast by the environmental light are utilized.

Figure 11C:
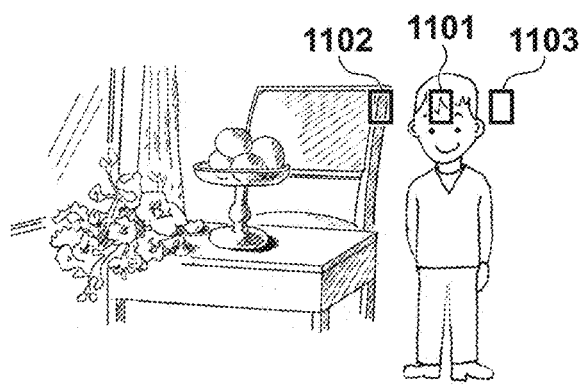
Figure 11D:
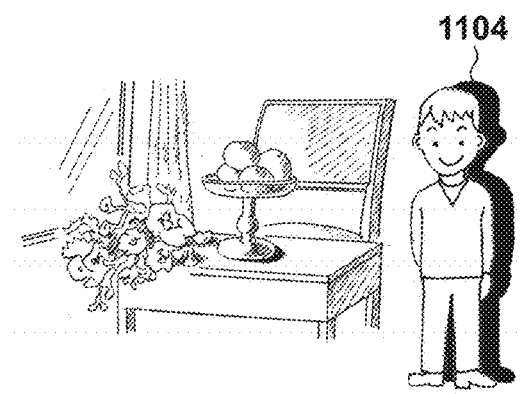

On the other hand, in the scene of FIG. 11C where the distance between the main object and the background (wall) is small (equal to or smaller than a threshold), strong auxiliary light casts a shadow 1104 of the main object on the background as shown in FIG. 11D. If the virtual light is added afterwards through the relighting processing, such a shadow will be inconsistent with shadows cast by the virtual light, thereby creating unnatural shadows in the resultant image. In addition, shadows cast by the auxiliary light are difficult to remove with the virtual light. Therefore, when the distance between the main object and the background is equal to or smaller than a threshold, the amount of light to be emitted by the auxiliary light source is made smaller than normal so as to hinder casting of significant shadows by the auxiliary light.

In this way, in a case where the relighting processing is impaired or unnatural shadows are cast by lighting up the main object with correct brightness using the auxiliary light source, the auxiliary light source emits weak light, and the amount of light is supplemented through the relighting processing.

On the other hand, when the depth of the main object is equal to or smaller than a threshold, or when the distance between the main object and the background is larger than a threshold, the auxiliary light source emits a normal amount of light as the auxiliary light is not likely to exert the above-described influence, and shadows are added through the relighting processing.

As described above, the present embodiment adopts a configuration in which the relighting processing parameters are determined using the distance information of the object. In this way, even in a scene where the effect of the auxiliary light has a possibility of rendering an image yielded from the relighting processing unnatural, the relighting processing can achieve correct brightness of the main object while making use of shadows cast by the environmental light.

Although the relighting processing parameters are determined using the distance information of the object in the present embodiment, the shadow information described in the first embodiment may be taken into consideration in addition to the distance information.

In this case, it is sufficient to add the process of step S504 according to the first embodiment, in which the degree of shadows of the object is determined, in a range from a point preceding step S1004 to a point following step S1005. That is to say, it is sufficient to execute the processes of steps S508 to S510 when the degree of shadows of the main object is higher than a predetermined value, when the depth of the main object is larger than a threshold, or when the distance between the main object and the background is equal to or smaller than a threshold.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-225436, filed on Nov. 5, 2014, which is hereby incorporated by reference herein in its entirety.

What is claimed is:

1. An image processing apparatus, comprising:
 a processor; and
 a memory storing a program which, when executed by the processor, causes the image processing apparatus to:
 apply, to an image that has been captured using an auxiliary light source, correction processing for adding an effect of a virtual light source; and
 determine an amount of light to be emitted by the auxiliary light source for capturing an is rage to which the correction processing is to be applied, and determines a parameter to be used in the correction processing,
 wherein
 the determinations of the amount of light to be emitted and the parameter are based on a degree of shadows of an object to be captured using the auxiliary light source, and
 wherein the correction processing is applied, to an image that has been captured using the auxiliary light source light emission of the determined amount in accordance with the determined parameter.

2. The image processing apparatus according to claim 1, wherein the program causes the image processing apparatus to
 determine the parameter such that shadows are to be added to the object in an image that are going to be captured using the auxiliary light source with light emission of the determined amount, through the correction processing.

3. The image processing apparatus according to claim 1, wherein
 the amount of light to be emitted and the parameter are determined based on a degree of shadows of the object in an image captured without using the auxiliary light source.

4. The image processing apparatus according to claim 1, wherein the program further causes the image processing apparatus to
calculate the degree of shadows based on luminance information of a region of the object in an image captured without using the auxiliary light source.

5. The image processing apparatus according to claim 1, wherein
when the degree of shadows of the object is equal to or lower than a predetermined value, a normal light emission amount is determined as the amount of light to be emitted by the auxiliary light source, the normal light emission amount achieving appropriate brightness of the object.

6. The image processing apparatus according to claim 5, wherein
when the degree of shadows of the object is equal to or lower than he predetermined value, the parameter is determined such that brightness of the object in an image in an image that are going to be captured using the auxiliary light source with light emission of the determined amount, is to be corrected through the correction processing after brightness of the image reduced.

7. The image processing apparatus according to claim 5, the program further causes the image processing apparatus to
obtain distance information of the object and a background, wherein
when a depth of the object is not determined to be equal to or smaller than a threshold based on the distance information, the parameter is determined similarly to a case in which the degree of shadows is larger than the predetermined value.

8. The image processing apparatus according to claim 7, wherein
when a difference between a distance to the object and a distance to the background is determined to be equal to or smaller than a threshold based on the distance information, the parameter is determined similarly to the ease in which the degree of shadows is larger than the predetermined value.

9. The image processing apparatus according to claim 7, wherein
when the depth of the object is determined to be equal to or smaller than the threshold and a difference between a distance to the object and a distance to the background is not determined to be equal to or smaller than a threshold based ort the distance information, the parameter is determined similarly to a case in which the degree of shadows as equal to or lower than the predetermined value.

10. The image processing apparatus according to claim 1, where
when the degree of shadows of the object is larger than a predetermined value, a light emission amount smaller than a normal light emission amount is determined as the amount of light to be emitted by the auxiliary light source, the normal light emission amount achieving appropriate brightness of the object.

11. The image processing apparatus according to claim 10, wherein
when the degree of shadows of the object is larger than the predetermined value, the parameter is determined such that brightness of the object in an image that are going to be captured using the auxiliary light source with light emission of the determined amount, is corrected through the correction processing without changing brightness of the image.

12. The image processing apparatus according to claim 10, wherein the program further causes the image processing apparatus to
determine, when the degree of shadows of the object is larger than the predetermined value, a position of the virtual light source to be used in the correction processing such that a direction of the virtual light source is the same as a direction of an environmental light source, the position being a part of the parameter.

13. The image processing apparatus according to claim 1, the program further causes the image processing apparatus to
obtain distance information of the object and a background, wherein
the amount of light to be emitted and the parameter are determined based on a degree of shadows estimated based on the distance information.

14. A method executed by an image processing apparatus, the method comprising:
applying, to an image that has been captured using an auxiliary light source, correction processing for adding an effect of a virtual light source;
determining (1) an amount of light to be emitted by the auxiliary light source for capturing an age to which the correction processing is to be applied, and (2) a parameter used in the correction processing,
wherein
in the determining, the amount of light to be emitted and the parameter are determined based on a degree of shadows of an object to be captured using the auxiliary light source, and
wherein the applying applies to the image that has been captured using the auxiliary light source with light emission of the amount determined by the determination unit, the correction processing in accordance with the parameter determined in the determining.

15. A non-transitory computer-readable recording medium storing a program for causing a computer provided in an image processing apparatus to execute a method comprising:
applying, to an image that has been captured using an auxiliary light source, correction processing, for adding an effect of a virtual light source;
determining (1) an amount of light to be emitted by the auxiliary light source for capturing an image to which the correction processing is to be applied, and (2) a parameter used in the correction processing,
wherein
in the determining, the amount of light to be emitted and the parameter are determined based on a degree of shadows of an object to be captured using the auxiliary light source, and
wherein the applying applies to the image that has been captured using the auxiliary light source with light emission of the amount determined by the determination unit, the correction processing in accordance with the parameter determined in the determining.

16. n image processing apparatus, comprising:
an image processing unit that performs a process for adding to an image captured using an auxiliary light source an effect of a virtual light source; and
a control unit that controls the auxiliary light source and the processing unit, wherein the control unit automatically sets any one of a plurality of modes including:

a first mode in which the control unit controls the auxiliary light source to emit light with a first light emission amount, and controls the image processing unit to add to a first image, which has been captured using the auxiliary light source emitted light with the first light emission amount, an effect of a first virtual light source from a predetermined direction; and a second node in which the control unit controls the auxiliary light source to emit light with a second light emission amount smaller than the first light emission amount, and controls the image processing unit to add to a second image which has been captured using the auxiliary light source emitted light with the second light emission amount an effect of a second virtual light source from a direction corresponding to a direction of an environmental light source of the second image.

17. The image capture apparatus according to claim 16, wherein the control unit controls the image processing unit in the first mode so as to reduce brightness of the first image, and then to add the effect of the first virtual light source to the first image of which the brightness is reduced.

18. The image capture apparatus according to claim 16, wherein the control unit controls the image processing unit in the second mode so as not to reduce brightness of the second image, and then to add the effect of the second virtual light source to the second image without of which the brightness is not reduced.

\* \* \* \* \*

UNITED STATES PATENT AND TRADEMARK OFFICE
CERTIFICATE OF CORRECTION

PATENT NO. : 9,936,141 B2
APPLICATION NO. : 14/927634
DATED : April 3, 2018
INVENTOR(S) : Kotaro Kitajima Page 1 of 1

It is certified that error appears in the above-identified patent and that said Letters Patent is hereby corrected as shown below:

In the Claims

Column 18, Line 42, delete "for capturing an is rage" and insert --for capturing an image--

Column 18, Line 51-52, delete "using the auxiliary light source light emission of the determined amount in accordance" and insert --using the auxiliary light source with light emission of the determined amount, in accordance--

Column 19, Line 19, delete "lower than he predetermined value," and insert --lower than the predetermined value,--

Column 19, Line 24-25, delete "brightness of the image reduced" and insert --brightness of the image is reduced--

Column 20, Line 28, delete "auxiliary light source for captuirng an age" and insert --auxiliary light source for capturing an image--

Column 20, Line 62, delete "n image processing apparatus, comprising:" and insert --An image processing apparatus, comprising:--

Column 21, Line 11, delete "a second node in which the control unit" and insert --a second mode in which the control unit--

Signed and Sealed this
Twenty-sixth Day of March, 2019

Andrei Iancu
*Director of the United States Patent and Trademark Office*